United States Patent
Cockayne et al.

(10) Patent No.: US 6,515,198 B2
(45) Date of Patent: Feb. 4, 2003

(54) USE OF PURINERGIC RECEPTOR MODULATORS AND RELATED REAGENTS

(75) Inventors: Debra Ann Cockayne, San Jose, CA (US); Anthony P. D. W. Ford, Mountain View, CA (US); Quan-Ming Zhu, Sunnyvale, CA (US); Wilhelm G. Lachnit, Burlingame, CA (US); Annika B. Malmberg, Palo Alto, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 09/783,067

(22) Filed: Feb. 13, 2001

(65) Prior Publication Data

US 2002/0165117 A1 Nov. 7, 2002

Related U.S. Application Data

(60) Provisional application No. 60/182,445, filed on Feb. 15, 2000, and provisional application No. 60/205,798, filed on May 17, 2000.

(51) Int. Cl.$^7$ .................... A01K 67/027; A01K 67/00; G01N 33/00
(52) U.S. Cl. ................. 800/18; 800/3; 800/9; 800/13
(58) Field of Search ............................ 800/3, 13, 9, 18

(56) References Cited

U.S. PATENT DOCUMENTS 6,207,876 B1 * 3/2001 Kellems et al.
6,214,581 B1 * 4/2001 Lynch et al.

FOREIGN PATENT DOCUMENTS

WO        WO99/36539        7/1999

OTHER PUBLICATIONS

Sigmund, C.D. 2000. Arterioscler Thromb Vasc Biol.20:1425–1429.*
Wall, R.J. 1996. Theriogenology 45:57–68.*
Souslova et al. 1997. Gene 195:101–111.*
Driessen et al. 1994. Brain research 666:182–188.*
Hashimoto and Kokubun. 1995. British Journal of Pharmacology 115:636–640.*
Bradley et al. 1992. Biotechnology 10:534–539.*
Campbell and Wilmut. 1997. Theriogenology 47:63–72.*
Mullins and Mullins. 1996. J. Clin. Invest. 97:1557–1560.*
Skepper, et al., "The Distribution of P2Xi and P2X3 Receptors in the Rat and Human Urinary Bladder," *Neurol. Urodynamics*, 18(4): Abstract 78.
Hegde, et al., "Evidence for Purinergic Neurotransmission in the Urinary Bladder of Pithed Rats," *European Journal of Pharmacology*, (1998), pp. 75–, vol. 349, Elsevier.

Bradbury, et al., "The Expression of P2X3 Purinoreceptors in Sensory Neurons: Effects of Axotomy and Glial–Derived Neurotrophic Factor," *Molecular & Cellular Neuroscience*, Nov. 1998, pp. 256–268, vol. 12(4–5).
Namasivayam, S. et al., "Purinergic Sensory Neurotransmission in the Urinary Bladder: an in vitro study in the Rat," *BJU International*, Nov. 1999, pp. 854–860, vol. 84(7).
Burnstock, Geoffrey, "Physiological and Pathological Roles of Purines: An Update," *Drug Development Research*, (1993), pp. 195–206, vol. 28, Wiley–Liss, Inc.
Chen, et al., "A P2X Purinoceptor Expressed by a Subset of Sensory Neurons," *Nature*, Oct. 5, 1995, pp. 428–431, vol. 377.
Zhong, et al., "Pharmacological and Molecular Characterization of P2X Receptors in Rat Pelvic Ganglion Neurons," *British Journal of Pharmacology*, (1998), pp. 771–781, vol. 125, Stockton Press.
Ferguson, et al., "ATP is Released from Rabbit Urinary Bladder Epithelial Cells by Hydrostatic Pressure Changes—a Possible Sensory Mechanism?", *Journal of Physiology*, (1997), pp. 503–511, vol. 505.
Lewis, et al., "Coexpression of P2X$_3$ Receptor Subunits Can Account for ATP–Gated Currents in Sensory Neurons," *NATURE*, Oct. 5, 1995, pp. 432–435, vol. 377.
Burnstock, G., Review: "The Past, Present and Future of Purine Nucleotides as Signalling Molecules," *Neuropharmacology*, (1997), pp. 1127–1139, vol. 36, No. 9, Elsevier Science, Ltd.
Souslova, et al., "Structure and Chromosomal Mapping of the Mouse P2X$_3$ Gene," *Gene*, Aug. 11, 1997, pp. 101–111, vol. 195.
Burnstock, G., "Release of Vasoactive Substances from Endothelial Cells by Shear Stress and Purinergic Mechanosensory Transduction," *Journal of Anatomy*, Apr. 1999, pp. 335–342, vol. 194 (Part 3).
Tsuda, at al., "Evidence for the Involvement of Spinal Endogenous ATP and P2X Receptors in Nociceptive Responses Caused by Formalin and Capsaicin in Mice," *British Journal of Pharmacology*, (1999), pp. 1497–1504, vol. 128, Stockton Press.

* cited by examiner

*Primary Examiner*—Remy Yucel
*Assistant Examiner*—Sita Pappu
(74) *Attorney, Agent, or Firm*—Sheela Mohan-Peterson; Rohan Peries

(57) ABSTRACT

The invention provides a method of treatment for an animal having a disease state associated with a genitourinary disorder with a purinergic receptor modulator. Also provided, is a transgenic animal having a disrupted purinergic receptor gene. The invention further provides for a method of screening using the transgenic animal as a positive control.

7 Claims, 3 Drawing Sheets

FIG. 1

P2X$_3$ Exon 1 KO Gene Targeting

Sma 1

↓

| CCCGGGATTG | GAGACCCCAC | CCCTGCTGTG | ACATCACAGG | GGAGTGGAGT | 50 |
| GAAGATGAAT | AAAAAGGTGG | TCCACCGCCC | TGGCCCTGGA | CTGTTGGCTT | 100 |
| CTAGAGTGTC | AAGAGGAGAG | ACGAGGCACT | GGACTACAGT | TGCCTGGCTT | 150 |
| ATAGGAACTG | GCTCTTTTCC | TCAAGCCCCA | TTAAGCAGCC | CACTCCAGTT | 200 |
| CTTGATCTCT | GTCTCCCAGT | CCTGAGGTCT | TTTCTCTCCT | TGGGCTGCAT | 250 |
| CCACAGCCTT | TCTGGGTGGC | TGTGAGCACT | TTCTCAGTAT | GAACTGTATA | 300 |
| TCAGACTTCT | TCACCTACGA | GACTACCAAG | TCGGTGGTTG | TGAAAAGCTG | 350 |
| GACCATTGGG | ATCATCAACC | GAGCCGTTCA | GCTGCTGATT | ATCTCCTACT | 400 |
| TTGTGGGGTG | AGTCCATGGT | CCTTCGGATG | GTGGGACAGA | AGGGCTACCT | 450 |
| GATGTCCTTC | CCTCCCTCTC | CAAGGCTGC | TCTGCAGCTC | CTAGACCCTC | 500 |
| TTCTCTGGGA | AACACTTTGA | TTTGTGGGAG | CCATGTCCTC | AGGATTGGCC | 550 |
| TCTGCCACTC | CCATCTAGAC | CCGTCTCAGG | TGCATTATTT | TACCCAGAAT | 600 |
| CTCTTCCAGG | ATTCTAGACA | CATACGCCAA | GAATATGAGT | CCATTCCCTG | 650 |
| GTTAAGAAAG | GACCCATATG | GTCCATCTTC | CCAGACCAAA | ACAAAACAA | 700 |
| AAACCAAGTC | AGACCCCTCC | CCACATTTCC | CCATTCCCCT | CCATTGAGTC | 750 |
| TTTAGAGTCC | CAGAAAGATA | AAGGAACGCA | GGAAGGAGGA | ATGAAAACCA | 800 |
| GGGAGATGGG | CTGATGTGTG | GAAGAAGAAC | CAGCTAGAGA | GGAAAGGGGA | 850 |
| GAGCTGGCTT | TAATGTAGAC | TTAGGAATTT | CTTCTTGTCA | TAGGGCTAGA | 900 |
| TGGTGAGAGG | TTAAAAAGCA | AGAGACATCT | GTTCTTGGAG | AGCAGGAGAA | 950 |
| CTGCCCCCCA | AGCTAGACAG | AGGCACAGAC | ACACTCAAGG | GAAGATCTGC | 1000 |
| CCAAGAGAAA | GGTACC | | | | 1016 |

↑
Kpn 1

*FIG. 4*

SEQUENCE LISTING

```
<160> NUMBER OF SEQ ID NOS: 1

<210> SEQ ID NO 1
<211> LENGTH: 1016
<212> TYPE: DNA
<213> ORGANISM: Mus musculus

<400> SEQUENCE: 1
```

-continued

| | | | | | |
|---|---|---|---|---|---|
| cccgggattg | gagacccac | ccctgctgtg | acatcacagg | ggagtggagt | gaagatgaat | 60 |
| aaaaaggtgg | tccaccgccc | tggccctgga | ctgttggctt | ctagagtgtc | aagaggagag | 120 |
| acgaggcact | ggactacagt | tgcctggctt | ataggaactg | gctcttttcc | tcaagcccca | 180 |
| ttaagcagcc | cactccagtt | cttgatctct | gtctcccagt | cctgaggtct | tttctctcct | 240 |
| tgggctgcat | ccacagcctt | tctgggtggc | tgtgagcact | ttctcagtat | gaactgtata | 300 |
| tcagacttct | tcacctacga | gactaccaag | tcggtggttg | tgaaaagctg | gaccattggg | 360 |
| atcatcaacc | gagccgttca | gctgctgatt | atctcctact | ttgtggggtg | agtccatggt | 420 |
| ccttcggatg | gtgggacaga | agggctacct | gatgtccttc | cctccctctc | ccaaggctgc | 480 |
| tctgcagctc | ctagaccctc | ttctctggga | aacactttga | tttgtgggag | ccatgtcctc | 540 |
| aggattggcc | tctgccactc | ccatctagac | ccgtctcagg | tgcattattt | tacccagaat | 600 |
| ctcttccagg | attctagaca | catacgccaa | gaatatgagt | ccattccctg | gttaagaaag | 660 |
| gacccatatg | gtccatcttc | ccagaccaaa | acaaaaacaa | aaaccaagtc | agaccctcc | 720 |
| ccacatttcc | ccattcccct | ccattgagtc | tttagagtcc | cagaaagata | aaggaacgca | 780 |
| ggaaggagga | atgaaaacca | gggagatggg | ctgatgtgtg | gaagaagaac | cagctagaga | 840 |
| ggaaagggga | gagctggctt | taatgtagac | ttaggaattt | cttcttgtca | tagggctaga | 900 |
| tggtgagagg | ttaaaaagca | agagacatct | gttcttggag | agcaggagaa | ctgccccca | 960 |
| agctagacag | aggcacagac | acactcaagg | gaagatctgc | ccaagagaaa | ggtacc | 1016 |

USE OF PURINERGIC RECEPTOR MODULATORS AND RELATED REAGENTS

CROSS-REFERENCE TO RELATED INVENTIONS

This application claims benefit under Title 35 U.S.C. 119(e) of U.S. Provisional Application No. 60/182,445, filed Feb. 15, 2000 and No. 60/205,798 filed May 17, 2000; all applications are hereby incorporated by reference in its entirety.

FIELD OF THE INVENTION

The present invention relates to a method of treating or preventing a disease state associated with a genitourinary or pain disorder using a purinergic receptor modulator. Also provided are transgenic or knockout animals deficient in a purinergic receptor and a method of screening for therapeutic compounds using the transgenic or knockout animals as positive controls.

BACKGROUND OF THE INVENTION

The urinary bladder is responsible for two important physiological functions: urine storage and urine emptying. This process involves two main steps: (1) the bladder fills progressively until the tension in its walls rises above a threshold level; and (2) a nervous reflex, called the micturition reflex, occurs that empties the bladder or, if this fails, at least causes a conscious desire to urinate. Although the micturition reflex is an autonomic spinal cord reflex, it can also be inhibited or mediated by centers in the cerebral cortex or brain.

Purines, acting via extracellular purinoreceptors, have been implicated as having a variety of physiological and pathological roles. (See, Burnstock (1993) *Drug Dev. Res.* 28:195–206.) ATP, and to a lesser extent, adenosine, can stimulate sensory nerve endings resulting in intense pain and a pronounced increase in sensory nerve discharge. ATP receptors have been classified into two major families, the P2Y- and P2X-purinoreceptors, on the basis of molecular structure, transduction mechanisms, and pharmacological characterization. The P2Y-purinoreceptors are G-protein coupled receptors, while the P2X-purinoreceptors are a family of ATP-gated cation channels. To date, cDNAs for seven P2X receptors subtypes have been cloned: $P2X_1$; $P2X_2$; $P2X_3$; $P2X_4$; $P2X_5$; $P2X_6$; and $P2X_7$. (See, Chen, et al. (1995) *Nature* 377:428–431; Lewis, et al. (1995) *Nature* 377:432–435; and Burnstock (1997) *Neurophamacol.* 36:1127–1139.) The structure and chromosomal mapping of mouse genomic $P2X_3$ receptor subunit has also been described. (See, Souslova, et al. (1997) *Gene* 195:101–111.) Purinergic receptors, in particular, P2X receptors, are known to form homomultimers or heteromultimers. In vitro, co-expression of $P2X_2$ and $P2X_3$ receptor subunits is necessary to produce ATP-gated currents with the properties seen in some sensory neurons. (See, Lewis, et al. (1995) *Nature* 377:432–435.)

Data exists suggesting that ATP may be released from epithelial/endothelial cells of various hollow organs, e.g., the urinary bladder, as a result of distention. (See, Burnstock (1999) *J. Anatomy* 194:335–342; and Ferguson et al. (1997) *J. Physiol.* 505:503–511.) Further studies propose that ATP released in this manner could serve a role in conveying information to sensory neurons located in subepithelial components, e.g., suburothelial lamina propria. (See Namasivayam, et al. (1999) *BJU Intl.* 84:854–860.) The P2X receptors have been studied in a number of neurons, including sensory, sympathetic, parasympathetic, mesenteric, and central neurons. (See, Zhong, et al. (1998) *Br. J. Pharmacol.* 125:771–781.) Recent evidence also suggests a role of endogenous ATP and purinergic receptors in nociceptive responses in mice. (See, Tsuda, et al. (1999) *Br. J. Pharmacol.* 128:1497–1504.)

However, while these studies suggest that purinergic receptors may play a role in afferent neurotransmission from the bladder, the exact molecular mechanism, i.e., the particular P2X receptor subunit or the involvement of this receptor subtype in the afferent control of the bladder, has yet to be defined.

The present invention fills this need by providing evidence that P2X receptor complexes, where the receptor complex comprises at lease one $P2X_3$ receptor subunit, play a critical role in relaying bladder filling information to the central nervous system. Therefore modulation of receptor complexes comprising at least one $P2X_3$ receptor subunit, either through antagonist- or agonist-mediated desensitization, may have utility in treating disease states associated with genitourinary disorders. Disease states associated with pain, in particular peripheral pain, inflammatory pain, or tissue injury pain can also be treated using a $P2X_3$ receptor subunit modulator.

SUMMARY OF THE INVENTION

The present invention provides a method of treating a subject having a disease state associated with a genitourinary or pain disorder comprising administering to the animal an effective amount of a purinoreceptor modulator. In further embodiments the genitourinary disorder is an overactive bladder, outlet obstruction, outlet insufficiency, or pelvic hypersensitivity. In a further embodiment, the pain disorder is peripheral pain, inflammatory pain, or tissue injury pain. In another embodiment the purinoreceptor modulator is a P2X receptor complex modulator. Preferably, the P2X receptor complex comprises at least one $P2X_3$ subunit. The present invention also provides that the P2X receptor complex modulator is an antagonist. In another embodiment the P2X receptor complex modulator is an agonist. In a further embodiment, the subject is a mammal, preferably a human.

The present invention encompasses a transgenic animal containing an altered allele for the gene that naturally encodes and expresses a functional $P2X_3$ purinoreceptor subunit. In another embodiment, the altered allele is a non-functional allele. In a further embodiment, the transgenic animal is a knockout (KO) animal. The KO animal has a phenotype, when compared to a wild-type control animal, which comprises: an increase in urinary bladder capacity; a lower frequency of urine voiding; larger voided volumes; and no significant change in cystometric pressure. In another embodiment, the KO animal has a phenotype when compared to a wild-type animal comprising attenuated nociception in response to ATP injection or attenuated nociception in response to formalin injection. In a further embodiment, KO transgenic animal is a mouse.

The present invention provides a method for selecting a potential therapeutic compound for use in the treatment of a disease state associated with a genitourinary disorder comprising: administering the compound to a wild-type animal or an animal having a disease state associated with a genitourinary disorder; measuring the resulting phenotype of the wild-type animal or the animal having the disease state; and comparing the resulting phenotype of the wild-type animal or the animal having the disease state to the phenotype of the KO animal.

The present invention further provides a method for selecting a potential therapeutic compound for use in the treatment of a disease state associated with a pain disorder comprising: administering the compound to a wild-type animal or an animal having a disease state associated with a pain disorder; measuring the resulting phenotype of the wild-type animal or the animal having the disease state; and comparing the resulting phenotype of the wild-type animal or the animal having the disease state to the phenotype of the KO animal.

BRIEF DESCRIPTION OF THE DRAWINGS

FIG. 4 shows the region of the $P2X_3$ receptor subunit gene deleted in the KO mouse (Sma I-Kpn I fragment). The sequence provided (SEQ ID NO:1) encompasses the genomic sequence from the Sma I site 5' of exon 1 to the Kpn I site of intron 1 (see arrows). SEQ ID NO:1 and FIG. 4 include all of exon 1 with the initiating ATG start codon at about nucleotides 55–57. Exon 1 runs from about nucleotide 55 through about nucleotide 225 (underlined).

DETAILED DESCRIPTION OF THE INVENTION

Before the present invention is described, it is to be understood that the present invention is not limited to the particular methodologies, protocols, cell lines, vectors, and reagents described, as these may vary. It is also understood that the terminology used herein is for the purpose of describing particular embodiments only, and is not to limit the scope of the present invention.

The singular forms "a," "an," and "the" include plural reference unless the context clearly dictates otherwise.

All technical and scientific terms used herein have the same meanings as commonly understood by one of ordinary skill in the art to which this invention pertains. The practice of the present invention will employ, unless otherwise indicated, conventional techniques of protein chemistry and biochemistry, molecular biology, microbiology and recombinant DNA technology, which are within the skill of the art. Such techniques are explained fully in the literature.

Although any machines, materials, and methods similar or equivalent to those described herein can be used to practice or test the present invention, the preferred machines, materials, and methods are now described. All patents, patent applications, and publications mentioned herein, whether supra or infra, are each incorporated by reference in their entirety.

Definitions "$P2X_3$ receptor subunit" refers to the amino acid sequences of substantially purified $P2X_3$ receptor subunit obtained from any species particularly mammalian species, including bovine, ovine, porcine, murine, equine, and preferably the human species, from any source, whether natural, synthetic, semi-synthetic, or recombinant.

"Agonist" refers to a molecule which, when bound to P2X receptor complex, or is within proximity of P2X receptor complex, modulates the activity of P2X receptor complex by increasing or prolonging the duration of the effect of P2X receptor complex. Agonists can include nucleotides, proteins, nucleic acids, carbohydrates, organic compounds, inorganic compounds, or any other molecules which modulate the effect of P2X receptor complex, in particular the $P2X_3$ receptor subunit.

"Amplification" relates to the production of additional copies of a nucleic acid sequence. Amplification can be carried out using polymerase chain reaction (PCR) technologies or other methods well known in the art.

"Antagonist" refers to a molecule which, when bound to P2X receptor complex or within close proximity, decreases the amount or the duration of the biological or immunological activity of P2X receptor complex. Antagonists may include proteins, nucleic acids, carbohydrates, antibodies, organic compounds, inorganic compounds, or any other molecules which exert an effect on P2X receptor complex activity, in particular the $P2X_3$ receptor subunit.

The term "antisense" refers to any composition containing nucleic acids which is complementary to the "sense" strand of a specific nucleic acid molecule. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

A "coding sequence" is a polynucleotide sequence that is transcribed into mRNA and translated into a polypeptide. The boundaries of the coding sequence are determined by a translation start codon at the 5'-terminus and a translation stop codon at the 3'-terminus. A coding sequence can include, but is not limited to, mRNA, cDNA, synthetic DNA, and recombinant polynucleotide sequences. Also included is genomic DNA where the coding sequence is interrupted by introns.

"Complementary" and "complementarity" refer to the natural binding of polynucleotides to other polynucleotides by base pairing. For example, the sequence "5' A-C-G-T 3'" will bind to the complementary sequence "3' T-G-C-A 5'." Complementarity between two single stranded molecules may be "partial," such that only some of the nucleic acids bind, or it may be "complete," such that total complementarity exists between the single stranded molecules.

The term "control elements" refers collectively to promoters, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

The phrase "correlates with expression of a polynucleotide" refers to the detection of the presence of nucleic acids, the same or related to a nucleic acid sequence encoding $P2X_3$ receptor subunit, e.g., by northern analysis or RT-PCR, is indicative of the presence of nucleic acids encoding $P2X_3$ receptor subunit in a sample, and thereby is indicative of the expression of the transcript from the polynucleotide encoding $P2X_3$ receptor subunit.

The phrase "detectably labeled" as used herein means joining, either covalently or non-covalently to the polynucleotides, polypeptides, or antibodies of the present invention, a substance which provides for a detectable signal. A wide variety of labels and conjugation techniques are well known in the art. Suitable labels include radionuclides, e.g., $^{32}P$, $^{35}S$, $^{3}H$, enzymes, substrates, cofactors, inhibitors, fluorescent moieties, chemiluminescent moieties, magnetic particles, and the like.

The phrase "disease state" means any disease, condition, symptom, disorder, or indication.

The phrase "disease state associated with a genitourinary disorder", which is used interchangeably with "symptoms associated with a genitourinary disorder", means disease states associated with the urinary tract including, but not limited to, overactive bladder, outlet obstruction, outlet insufficiency, and pelvic hypersensitivity. In particular, the compounds of the present invention may be useful in the treatment of symptoms associated with the above disease state, e.g., urgency, frequency, altered bladder capacity, incontinence, micturition threshold, unstable bladder contractions, sphincteric spasticity, detrusor hyperreflexia (neurogenic bladder), detrusor instability, benign prostatic hyperplasia (BPH), urethral stricture disease, tumors, low flow rates, difficulty in initiating urination, urgency, suprapubic pain, urethral hypermobility, intrinsic sphincteric deficiency, mixed incontinence, stress incontinence, pelvic pain, interstitial (cell) cystitis, prostadynia, prostatis, vulvadynia, urethritis, orchidalgia, and other symptoms related to overactive bladder.

The phrases "effective amount" or "therapeutically effective amount" mean a concentration of P2X receptor complex modulator sufficient to inhibit or enhance the effect of the P2X receptor complex.

The term "expression" as used herein intends both transcriptional and translational processes, i.e., the production of messenger RNA and/or the production of protein therefrom.

The term "modulate" refers to a change in the activity of P2X receptor complex which contains at least one $P2X_3$ receptor subunit. For example, modulation may cause an increase or a decrease in protein activity, binding characteristics, ion channel opening and conductance, receptor or second messenger signaling, or any other biological, functional, or immunological properties of P2X receptor complex. The term "modulator" is a composition having the ability to effect the above changes. The ability to modulate the activity of $P2X_3$ receptor can be exploited in assays to screen for organic, inorganic, or biological compounds which affect the above properties of P2X receptor complex, in particular the $P2X_3$ receptor subunit.

"Nociceptor" refers to a receptor for pain caused by injury to body tissues; the injury may be from physical stimuli such as mechanical, thermal, or electrical stimuli, or from chemical stimuli such as the presence of a toxin or a an excess of a non-toxic substance, e.g., ATP or formalin. The term "nociception" refers to the sensing of pain through these receptors.

"Nocifensor" refers to a system of nerves in the skin and mucous membranes which are concerned with local defense against injury. "Nocifensive behavior" refers to pain related behavior in response to mechanical, thermal, electrical, or chemical stimuli, e.g., hindpaw lifting in rats.

"Nucleic acid" and "nucleic acid sequence" refer to a nucleotide, oligonucleotide, polynucleotide, or any fragment thereof. These phrases also refer to DNA or RNA of genomic or synthetic origin which may be single stranded or double stranded and may represent the sense of the antisense strand, a peptide nucleic acid (PNA), or any DNA-like or RNA-like material. In this context, "fragments" refer to those nucleic acids which, when translated, would produce polypeptides retaining some functional characteristic, e.g., antigenicity, or structural domain, e.g., ion channel domain, characteristic of the full-length polypeptide.

The terms "operably associated" and "operably linked" refer to functionally related but heterologous nucleic acid sequences. A promoter is operably associated or operably linked with a coding sequence if the promoter controls the translation or expression of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

An "oligonucleotide" refers to a nucleic acid molecule of at least about 6 to 50 nucleotides, preferably about 15 to 30 nucleotides, and more preferably 20 to 25 nucleotides, which can be used in PCR amplification or in a hybridization assay. "Oligonucleotide" is substantially equivalent to the terms "amplimer," "primer," "oligomer," and "probe" as these terms are commonly defined in the art.

The term "outlet obstruction" refers to disease states including, but not limited to, benign prostatic hyperplasia (BPH), urethral stricture disease, tumors, etc. Outlet obstruction can be further defined as obstructive (e.g., low flow rates, difficulty initiating urination, etc.) or irritative (e.g., urgency, suprapubic pain, etc.).

The term "outlet insufficiency" refers to urethral hypermobility or intrinsic sphincteric deficiency and is symptomatically manifested as stress inconinence.

The terms "overactive bladder" or "detrusor hyperactivity" refer to symptoms which manifest as urgency, frequency, and/or incontinence episodes. These symptoms can be caused by changes in bladder capacity, micturition threshold, unstable bladder contractions, and/or sphincteric spasticity. Hyperreflexia, outlet obstruction, outlet insufficiency, and pelvic hypersensitivity can also be idiopathic for this disease state.

"Pain" means the more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, tissue injury pain, and the like (*Dorland's Illustrated Medical Dictionary*, 28th Edition, W. B. Saunders Company, Philadelphia, Pa.). The goal of treatment of pain is to reduce the degree or severity of pain perceived by a treatment subject.

The term "pelvic hypersensitivity" refers to pelvic pain, incontinence, prostadynia, prostatis, vulvadynia, urethritis, orchidalgia, etc. Pelvic hypersensitivity can be manifested as pain or discomfort in the pelvic region and also usually includes symptoms of overactive bladder defined above.

The term "phenotype" refers to the physical, biochemical, and physiological makeup of an animal as determined both genetically and environmentally. As used herein, the phrase "resulting phenotype" refers to a wild-type animal or an animal having a disease state associated with a genitourinary disorder treated with a potential therapeutic compound which results in a phenotype similar to that of a KO animal.

"Recombinant host cells," "host cells," "cells," "cell lines," "cell cultures," and other such terms denoting cell lines cultured as unicellular entities refer to cells which can be, or have been, used as recipients for recombinant vectors or other transfer DNA, immaterial of the method by which the DNA is introduced into the cell or the subsequent disposition of the cell. The terms include the progeny of the original cell which has been transfected. Cells in primary culture as well as cells such as oocytes also can be used as recipients.

A "reporter gene" is a gene that, upon expression, confers a phenotype on a cell expressing the reporter gene, such that the cell can be identified under appropriate conditions. For example, the reporter gene may produce a polypeptide product that can be easily detected or measured in a routine assay. Suitable reporter genes known in the art which confer this characteristic include those that encode chloramphenicol acetyl transferase (CAT activity), βgalactosidase, luciferase, alkaline phosphatase, human growth hormone, fluorescent proteins, such as green fluorescent protein (GFP), and others. Indeed, any gene that encodes a protein or enzyme that can readily be measured, for example, by an immunoassay such as an enzyme-linked immunosorbent assay (ELISA) or by the enzymatic conversion of a substrate into a detectable product, and that is substantially not expressed in the host cells (specific expression with no background) can be used as a reporter gene to test for promoter activity. Other reporter genes for use herein include genes that allow selection of cells based on their ability to thrive in the presence or absence of a chemical or other agent that inhibits an essential cell function. Suitable markers, therefore, include genes coding for proteins which confer drug resistance or sensitivity thereto, or change the antigenic characteristics of those cells expressing the reporter gene when the cells are grown in an appropriate selective medium. For example, reporter genes include: cytotoxic and drug resistance markers, whereby cells are selected by their ability to grow on media containing one or more of the cytotoxins or drugs; auxotrophic markers by which cells are selected by their ability to grow on defined media with or without particular nutrients or supplements; and metabolic markers by which cells are selected for, e.g., their ability to grow on defined media containing the appropriate sugar as the sole carbon source. These and other reporter genes are well known in the art.

A "change in the level of reporter gene product" is shown by comparing expression levels of the reporter gene product in a cell exposed to a candidate compound relative to the levels of reporter gene product expressed in a cell that is not exposed to the test compound and/or to a cell that is exposed to a control compound. The change in level can be determined quantitatively for example, by measurement using a spectrophotometer, spectrofluorometer, luminometer, and the like, and will generally represent a statistically significant increase or decrease in the level from background. However, such a change may also be noted without quantitative measurement simply by, e.g., visualization, such as when the reporter gene is one that confers the ability of cells to form colored colonies on chromogenic substrates, or the ability of cells to thrive and/or die in the presence of test compounds.

"Subject" or "animal" means mammals and non-mammals. Mammals means any member of the Mammalia class including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, reptiles, and the like. The term "subject" does not denote a particular age or sex.

The term "transfection" refers to the insertion of an exogenous polynucleotide into a host cell, irrespective of the method used for the insertion, or the molecular form of the polynucleotide that is inserted. The insertion of a polynucleotide per se and the insertion of a plasmid or vector comprised of the exogenous polynucleotide are included. The exogenous polynucleotide may be directly transcribed and translated by the cell, maintained as a nonintegrated vector, for example, a plasmid, or alternatively, may be stably integrated into the host genome.

The term "transformed" refers to any known method for the insertion of foreign DNA or RNA sequences into a host prokaryotic cell. The term "transfected" refers to any known method for the insertion of foreign DNA or RNA sequences into a host eukaryotic cell. Such transformed or transfected cells include stably transformed or transfected cells in which the inserted DNA is rendered capable of replication in the host cell. They also include transiently expressing cells which express the inserted DNA or RNA for limited periods of time. The transformation or transfection procedure depends on the host cell being transformed. It can include packaging the polynucleotide in a virus as well as direct uptake of the polynucleotide, such as, for example, lipofection, electroporation, or microinjection. Transformation and transfection can result in incorporation of the inserted DNA into the genome of the host cell or the maintenance of the inserted DNA within the host cell in plasmid form. Methods of transformation are well known in the art and include, but are not limited to, viral infection, electroporation, lipofection, and calcium phosphate mediated direct uptake.

The term "transgenic animal" or "knockout animal" can refer to an engineered animal having dysfunctional expression of a target gene or genes.

"Treating" or "treatment of" a disease state includes: 1) preventing the disease state, i.e. causing the clinical symptoms of the disease state not to develop in a subject that may be exposed to or predisposed to the disease state, but does not yet experience or display symptoms of the disease state; 2) inhibiting the disease state, i.e., arresting the development of the disease state or its clinical symptoms; 3) or relieving the disease state, i.e., causing temporary or permanent regression of the disease state or its clinical symptoms.

A "vector" is a replicon in which another polynucleotide segment is attached, such as to bring about the replication and/or expression of the attached segment. The term includes expression vectors, cloning vectors, and the like.

The phrase "without a significant increase in cystometric pressure" refers to comparative values, which are obtained from the measurement of bladder pressure and capacity in response to filling, between a knockout animal and a wild-type control animal. A significant increase would be a value higher than the 95% confidence limit.

The Invention

The present invention is based on the discovery that disruption of the gene encoding the $P2X_3$ receptor subunit in a gene knockout (KO) animal, results in increased urinary bladder capacity, less frequent urine voiding (e.g., approximately two-fold longer interval between voiding when compared to a wild-type control mouse), and larger voided volumes (e.g., approximately two-fold higher when compared to a wild-type control mouse), all without a significant increase in cystometric pressure. Therefore, P2X receptor complex modulators will be useful in the treatment or prevention of disease states associated with various genitourinary disorders, where the P2X receptor complex comprises at least one $P2X_3$ receptor subunit.

KO mice deficient in the $P2X_3$ receptor subunit were generated using techniques described below. Cystometry, or the measurement of bladder pressure and capacity in response to filling, was subsequently examined in these KO mice and wild-type control mice.

Recent studies have localized the P2X$_3$ receptor subunit to nociceptive sensory nerves as well as nerve fibers associated with the urinary bladder. (See, Elneil, et al. (1999) *Neurourol. Urodynamics* 18(4):abstract 78; Hegde, et al. (1998) *Eur. J. Pharmacol.* 349:75–82; and Bradbury, et al. (1998) *Mol. Cell. Neurosci.* 12:256–268.) Additionally, agents capable of desensitizing P2X$_3$ receptor subunit responses (e.g., αβ-ATP, suramin) have also been shown to decrease the activity of bladder sensory afferents. (See, Namasivayam, et al. supra.)

Taken together, the above data suggests that P2X receptor complex modulators should be useful in regulating the afferent signaling pathways from the urinary bladder to the CNS, where the P2X receptor complex comprises at least one P2X$_3$ receptor subunit. These modulators are therefore useful in the treatment of disease states associated with genitourinary disorders including, but not limited to, overactive bladder, outlet obstruction, outlet insufficiency, and pelvic hypersensitivity. In particular, the compounds of the present invention may be useful in the treatment of symptoms associated with the above disease state, e.g., urgency, frequency, altered bladder capacity, incontinence, micturition threshold, unstable bladder contractions, sphincteric spasticity, detrusor hyperreflexia (neurogenic bladder), detrusor instability, benign prostatic hyperplasia (BPH), urethral stricture disease, tumors, low flow rates, difficulty in initiating urination, urgency, suprapubic pain, urethral hypermobility, intrinsic sphincteric deficiency, mixed incontinence, stress incontinence, pelvic pain, interstitial (cell) cystitis, prostadynia, prostatis, vulvadynia, urethritis, orchidalgia, and other symptoms related to overactive bladder.

Further studies revealed that P2X$_3$ KO mice exhibit attenuated nociceptive responses to injection of ATP and formalin. The attenuation of nociception in response to ATP was dose-dependent, with 77% inhibition at 100 nmol ATP and 45% inhibition at 500 nmol ATP.

The formalin test is used to evaluate nociception resulting from the injection of a dilute formalin solution into the hindpaw of mice. Formalin injection elicits two phases of nociceptive behavior: an early transient phase (5 minutes post-injection); and a late persistent phase (15–30 minutes post-injection). It has been suggested that the first phase is attributable to direct stimulation of primary afferent fibers (neurogenic pain) while the second phase is a result of peripheral inflammation (inflammatory pain). Recent studies indicate that formalin evokes a continuous nociceptive response generated by injured tissue, thus activating various regulatory substances, e.g., ATP. (See, Tsuda, supra.)

P2X$_3$ KO mice exhibited attenuated nociception in response to formalin as measured by hindpaw lifting. The hindpaw lifting responses in both phases were reduced by approximately 50%, suggesting a role for ATP activation of the P2X$_3$ receptor subunit in tissue injury pain. Therefore modulators of P2X3 receptor subunit would be useful in the treatment of pain including, but not limited to, peripheral pain, inflammatory, or tissue injury pain.

Transgenic Animals

The present invention also encompasses transgenic animals with altered P2X$_3$ receptor subunit activity. Recombinant clones derived from the genomic sequences, e.g., containing introns, will be useful for transgenic and knockout studies, including transgenic cells, organisms, and knockout animals, and for gene therapy. (See, e.g., Goodnow (1992) "Transgenic Animals" in Roitt (ed.) Encyclopedia of Immunology, Academic Press, San Diego, Calif., pp. 1502–1504; Travis (1992) Science 254:707–710; Capecchi (1989) Science 244:1288–1292; Robertson (ed.) (1987) Teratocarcinomas and Embryonic Stem Cells: A Practical Approach, IRL Press, Oxford; Rosenberg (1992) J. Clinical Oncology 10:180–199; Hogan, et al. (eds.) (1994) Manipulating the Mouse Embryo: A Laboratory Manual, 2nd edition, Cold Spring Harbor Press, NY; Wei (1997) Ann. Rev. Pharmacol. Toxicol. 37:119–141; and Rajewsky, et al. (1996) J. Clin. Inves. 98:S51–S53.)

Examples of these techniques include: 1) Insertion of normal or mutant versions of DNA encoding P2X$_3$ receptor subunit or homologous animal versions of these genes, by microinjection, retroviral infection, or other means well known to those skilled in the art, into appropriate fertilized embryos in order to produce a transgenic animal (see, e.g., Hogan, supra); and 2) homologous recombination (see, e.g., Capecchi, supra; and Zimmer and Gruss (1989) Nature 338:150–153) into embryonic stem cells allowing for the introduction of mutant or normal, human or animal versions of genes into the germlne of an animal. Resulting KO animals can have altered regulation of expression or structure of P2X$_3$ receptor subunit.

The technique of homologous recombination is well known in the art. It replaces the native gene with the inserted gene, in the animal genome, and is thus useful for producing an animal that cannot express native receptor but does express, for example, no receptor, an inserted mutant receptor, or an alternative form of the receptor.

With respect to creation of transgenic animals, microinjection adds genes to the genome, but does not remove them, and so is useful for producing an animal which expresses its own and added receptors, resulting in overexpression of the receptor. One means available for producing a transgenic animal, with a mouse as an example, is as follows: Female mice are mated, and the resulting fertilized eggs are dissected out of their oviducts. The eggs are stored in an appropriate medium such as M2 medium (see, e.g., Hogan, supra). DNA or cDNA encoding P2X$_3$ receptor subunit is purified from an appropriate vector by methods well known in the art. Inducible promoters may be fused with the coding region of the DNA to provide an experimental means to regulate expression of the transgene. Alternatively, or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

A method of screening for a compound having P2X receptor complex modulator activity using the P2X$_3$ receptor subunit KO animal of the present invention and/or additional transgenic models is also contemplated. Since the normal action of receptor-specific drugs is to activate or to inhibit the receptor, the transgenic animal model systems described above are useful for testing the biological activity of drugs directed against the P2X$_3$ receptor subunit even before such drugs become available. In particular, these animal model systems are useful for predicting or evaluating possible therapeutic applications of drugs which activate or inhibit the P2X receptor complex, where the receptor complex comprises at least one $P2X_3$ receptor subunit. The transgenic animals which over- or underproduce $P2X_3$ receptor subunit indicate, by their physiological state, whether over- or underproduction of $P2X_3$ receptor subunit would be therapeutically useful. It is therefore useful to utilize the transgenic model systems to evaluate therapeutic action.

As the present invention illustrates, $P2X_3$ receptor subunit knockout animals have phenotypic characteristics including, but not limited to, larger bladder capacity, lower frequency of urine voiding, larger voided volumes, and similar cystometric pressure values, in comparison to wild-type control animals. Thus, an animal, which does not express the $P2X_3$ receptor subunit (a KO animal), is useful as a positive control for evaluating potential therapeutic compounds. Compounds that cause wild-type animals or animals having disease states described above to express phenotypic characteristics similar to that of the KO animal should be useful in the treatment of these disease states.

Similarly, a transgenic animal, which overproduces the $P2X_3$ receptor subunit, is useful as a test model for potential therapeutic compounds. These compounds will typically alleviate the symptoms of the disease states described above.

Therapeutics and Pharmaceutical Uses

As noted above, the present invention provides a method of treating a subject having a disease state associated with a genitourinary disorder. Genitourinary disorders include, but are not limited to, overactive bladder, outlet obstruction, outlet insufficiency, and pelvic hypersensitivity. In particular, the compounds of the present invention may be useful in the treatment of symptoms associated with the above disease state, e.g., urgency, frequency, altered bladder capacity, incontinence, micturition threshold, unstable bladder contractions, sphincteric spasticity, detrusor hyperreflexia (neurogenic bladder), detrusor instability, benign prostatic hyperplasia (BPH), urethral stricture disease, tumors, low flow rates, difficulty in initiating urination, urgency, suprapubic pain, urethral hypermobility, intrinsic sphincteric deficiency, mixed incontinence, stress incontinence, pelvic pain, interstitial (cell) cystitis, prostadynia, prostatis, vulvadynia, urethritis, orchidalgia, and other symptoms related to overactive bladder. Also provided is a method of treating an subject having a disease state associated with pain including, but not limited to, peripheral pain, inflammatory pain, or tissue injury pain. These and other therapeutic uses are described, e.g., in Goodman & Gilman's, (1996) *The Pharmacological Basis of Therapeutics*, $9^{TH}$ ed., McGraw-Hill, New York, Chapter 26:601–616; and Coleman, R. A. (1994) *Pharmacol. Revs.* 46:205–229.

In general, $P2X_3$ receptor complex modulators may be administered in a therapeutically effective amount by any of the accepted modes of administration for agents that serve similar utilities. Suitable dosage ranges are typically 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able to ascertain a therapeutically effective amount of the compounds of the present invention for a given disease. For example frequency of dosing can be 1, 2, 3, or multiple times per day.

In general, $P2X_3$ receptor complex modulators may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

$P2X_3$ receptor complex modulators, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

$P2X_3$ receptor complex modulators may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

$P2X_3$ receptor complex modulators can be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

$P2X_3$ receptor complex modulators may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

$P2X_3$ receptor complex modulators may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

$P2X_3$ receptor complex modulators can be formulated for vaginal administration. Pessaries, tampons, creams, gels, pastes, foams or sprays containing in addition to the active ingredient such carriers as are known in the art to be appropriate.

$P2X_3$ receptor complex modulators may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

$P2X_3$ receptor complex modulators can be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, dichlorotetrafluoroethane, carbon dioxide, or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Martin (ed.) (1995) *Remington: The Science and Practice of Pharmacy,* 19th ed., Mack Publishing Company, Easton, Pa.

All patents, patent applications, and publications mentioned herein, whether supra or infra, are each incorporated by reference in its entirety. The broad scope of this invention is best understood with reference to the following examples, which are not intended to limit the invention to the specific embodiments described below.

EXAMPLES

Some of the standard methods are described or referenced, e.g., in Maniatis et al. (1982) *Molecular Cloning: A Laboratory Manual,* Cold Spring Harbor Laboratory, Cold Spring Harbor Press; Sambrook et al. (1989) *Molecular Cloning: A Laboratory Manual,* (2d ed.), vols. 1–3, CSH Press, N.Y.; or Ausubel et al. (1987 and Supplements) *Current Protocols in Molecular Biology,* Greene/Wiley, New York; Innis et al. (eds.)(1990) *PCR Protocols: A Guide to Methods and Applications,* Academic Press, N.Y. Methods for protein purification include such methods as ammonium sulfate precipitation, column chromatography, electrophoresis, centrifugation, crystallization, and others. See, e.g., Ausubel et al. (1987 and periodic supplements); Deutscher (1990) "Guide to Protein Purification" in *Methods in Enzymol.,* vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering Principle and Methods,* Plenum Press, NY, 12:87–98; and Crowe et al. (1992) OIAexpress: The High Level Expression & Protein Purification System QUIAGEN, Inc., Chatsworth, Calif.

Example I

Generation of $P2X_3$ Receptor Subunit-deficient Mice

Figure 1:
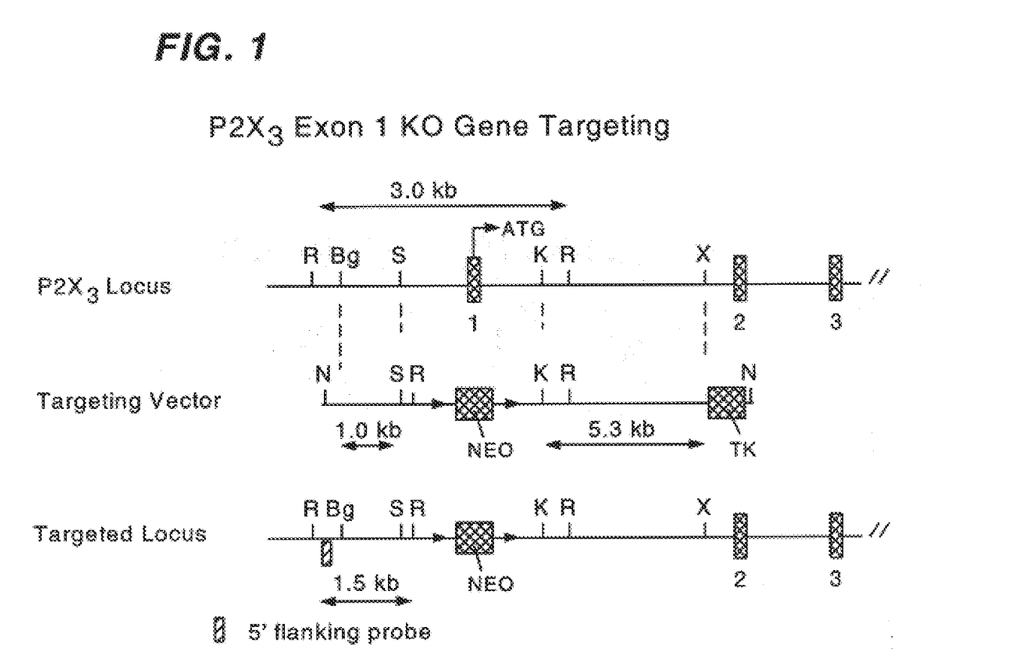
FIG. 1 shows a linear representation of the intact $P2X_3$ receptor subunit locus, the targeting vector used for disruption of the $P2X_3$ receptor subunit locus, and the result of homologous recombination between the targeting vector and the endogenous $P2X_3$ receptor subunit locus.
Figure 4:
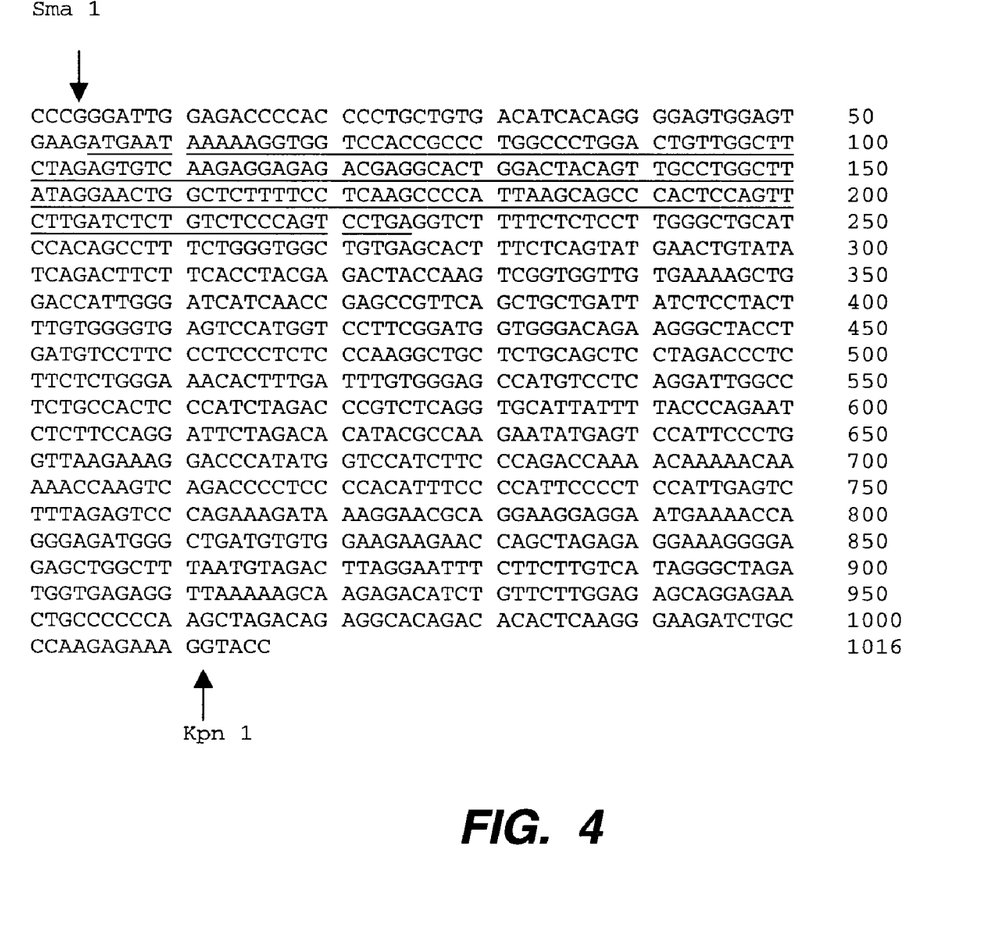

The $P2X_3$ gene was cloned from a mouse ES-129/Ola P1 genomic library (Genome Systems, St. Louis, Mo.), and genomic subclones were generated. The $P2X_3$ targeting vector included a total of 6.3 kb of genomic sequence, a loxP flanked neomycin resistance gene, and the HSV-TK gene. Homologous recombination between the targeting vector and the wild type $P2X_3$ allele resulted in a deletion of 1.0 kb of the $P2X_3$ gene, including exon 1 and the initiating ATG (see, sequence defined by Sma I-Kpn I fragment in FIG. 4). This sequence was replaced with the loxP flanked neomycin resistance gene (see, FIG. 1).

Figure 2:
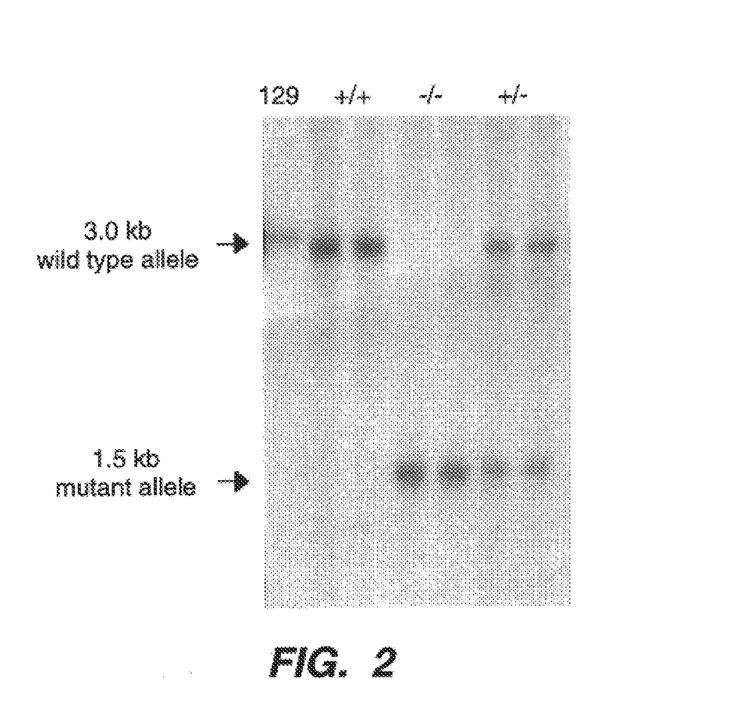
FIG. 2 shows a diagnostic Southern blot used to identify $P2X_3$ wild-type and KO animals. Using a 140 bp 5' flanking region probe, the wild-type mice (+/+) yielded the predicted 3.0 kb EcoRI fragment indicative of a wild-type allele, while the knockout (KO) mice (−/−) yielded the predicted 1.5 kb EcoRI fragment indicative of a mutant $P2X_3$ allele.

A Not I linearized targeting vector was electroporated into 129Ola-derived E14-1 embryonic stem (ES) cells, and clones were selected in 310 mg/ml active G418 (Gibco BRL, Gaithersburg, Md.) and 2 mM gancyclovir (Roche Pharmaceuticals). Positive clones were identified by Southern blot analysis using a 140 bp 5' flanking region probe to screen for the predicted 3.0 kb and 1.5 kb EcoRI fragments, which were indicative of the wild type and mutant $P2X_3$ alleles (see, FIG. 2). Four correctly targeted clones were identified out of 346 clones screened.

Targeted clones were subsequently injected into C57Bl/6 (Harlan) blastocysts, and chimeras were established. Germ-line transmission of the targeted allele was established by mating chimeras to C57Bl/6 (Harlan) mice. All mice analyzed in this study were of the 129OlaxC57Bl/6 (Harlan) genetic background, and were derived from homozygous F2 crosses.

$P2X_2$ KO mice are generated as described above and are used to further evaluate the present invention.

Example II

Bladder Cystometry

Mice used for these studies were produced from F2 homozygous crosses of $P2X_3$ receptor subunit +/+ and $P2X_3$ receptor subunit –/– mice (described above) and were approximately 5 months of age. Mice were anesthetized with isoflurane (Baxter Healthcare Corp, Deerfield, Ill.) and placed on a warm pad. In preparation for surgery the animals were administered Amoxicillin (10 mg/animal) and Lactated Ringers Solution (1 ml/animal) subcutaneously, and the abdomen and the back of the neck were shaved and scrubbed with Nolvasan (Fort Dodge Animal Health, Fort Dodge, Iowa).

A midline abdominal incision was made and the bladder was exposed. A small hole was made at the dome of the bladder, and a fluid-filled PE-10 tube (Becton Dickinson, Sparks, Md.) was inserted and ligated with 5-0 Tevdek suture (Deknatel DSP, Fall River Mass.). The cannula was tuned subcutaneously to the back of the neck, and the incision was closed with 4-0 silk (Ethicon Inc, Somerville, N.J.) and wound clips. The bladder catheter was secured with 4-0 silk and placed under the skin. Mice were returned to normal caging and allowed to recover from surgery.

Cystometry was performed 7 days after bladder cannulation. Each mouse was placed in a restraint box placed within a metabolic cage. Saline was infused into the bladder, at a rate of 3 ml/hour, through the bladder catheter following connection to a pressure transducer via a 3-way tap. The bladder pressure (voiding pressure) and void volumes were recorded with a Grass model 7 polygraph (Grass Instrument Company, Quincy, Mass.). At the end of the experiment mice were euthanized by $CO_2$ narcosis.

Figure 3:
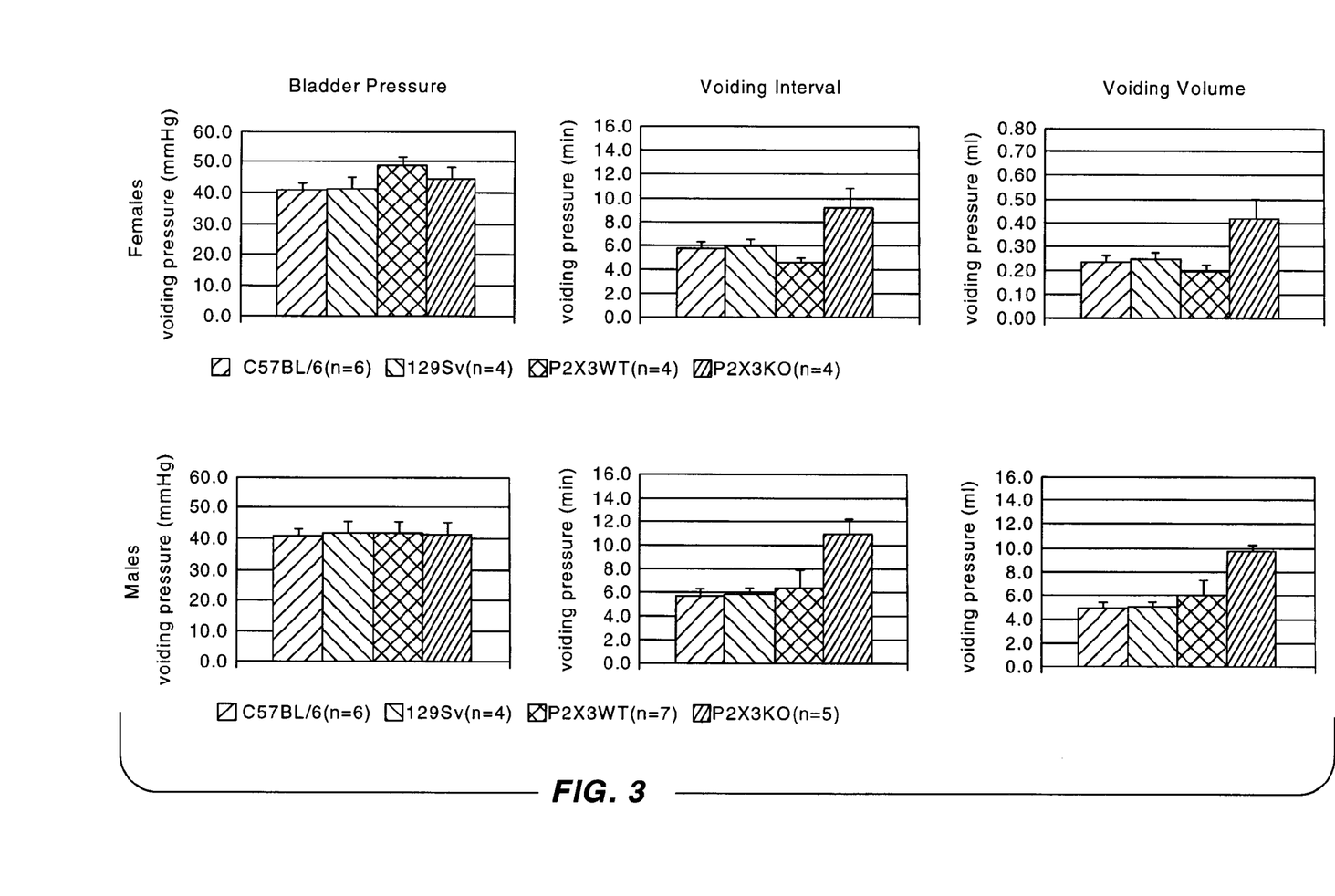
FIG. 3 shows the results of bladder cystometry studies on male and female $P2X_3$ wild-type and $P2X_3$ KO mice, as well as controls for genetic background.

Results of the above cystometry studies indicated that $P2X_3$ receptor subunit KO mice had larger bladder capacities when compared to their wild-type counterparts. The measured cystometric pressure was not significantly different between wild type and KO mice. This finding is of note in view of the large voided volumes and low frequency of micturition observed in the KO mice (see FIG. 3).

Example III

Measurement of Nociceptive Responses

ATP was administered to 2–3 month old P2X3 wild-type and KO mice via intraplantar injection of varying doses of ATP (e.g., 100–500 nmol.) in a total volume of 20 ul. Hindpaw lifting was measured to assess nociceptive responses. As noted above, inhibition of this response was 77% at 100 nmol ATP and 45% at 500 nmol.

Hindpaw lifting and licking was measured in 3–4 month old P2X3 wild-type and KO mice following intraplanar injection of 5% formalin in a total volume of 20 ul. (Hunskaar, et al. (1985) *J. Neurosci. Methods* 14:69–76.) As noted above, nociceptive responses were attenuated in both phases of the formalin test.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A transgenic mouse containing an altered allele for the gene that naturally encodes and expresses a functional P2X$_3$ receptor subunit, wherein the altered allele is a nonfunctional P2X$_3$ allele, and wherein said mouse, as a result of having a nonfunctional P2X$_3$ allele, has a reduction in an afferent signaling pathway from the bladder to the central nervous system, wherein said mouse is homozygous for said non-functional P2X$_3$ allele.

2. The transgenic mouse of claim 1, wherein the phenotype of the transgenic mouse relative to a wild-type control mouse comprises:
   a) an increase in urinary bladder capacity;
   b) a lower frequency of urine voiding;
   c) a larger voided volume; and
   d) no significant change in cystometric pressure.

3. The transgenic mouse of claim 1, wherein the phenotype of the transgenic mouse relative to a wild-type control mouse comprises:
   a) attenuated nociception in response to injection of ATP; or
   b) attenuated nociception in response to injection of formalin.

4. A method for selecting a potential therapeutic compound for use in the treatment of a disease state associated with a genitourinary disorder comprising:
   a) administering the compound to a wild-type mouse or a mouse having a disease state associated with a genitourinary disorder;
   b) measuring the resulting phenotype of wild-type mouse or a mouse having the disease state; and
   c) comparing the resulting phenotype of the wild-type mouse or a mouse having the disease state to the phenotype of the transgenic mouse of claim 2, wherein the phenotype is selected from the group consisting of urinary bladder capacity, frequency of urine voiding, cystometric pressure, and voided volume.

5. A method for selecting a potential therapeutic compound for use in the treatment of a disease state associated with a pain disorder comprising:
   a) administering the compound to a wild-type animal or an animal having a disease state associated with a pain disorder;
   b) measuring the resulting phenotype of wild-type animal or the animal having the disease state; and
   c) comparing the resulting phenotype of the wild-type animal or the animal having the disease state to the phenotype of the knockout animal of claim 3, wherein the phenotype is attenuated nociception involving a P2X$_3$ receptor subunit.

6. A method of producing a transgenic mouse in which one or both alleles of an endogenous P2X$_3$ are disrupted, the method comprising:
   a) introducing into embryonic stem (ES) cells a P2X$_3$ transgene, said transgene comprising a disrupted P2X$_3$ gene, such that an endogenous P2X$_3$ allele is disrupted;
   b) selecting ES cells comprising said disrupted P2X$_3$ allele, thereby producing modified ES cells;
   c) introducing said modified ES cells into mouse blastocysts, producing a chimeric blastocysts;
   d) transferring said chimeric blastocysts into a pseudopregnant mice; and
   e) identifyng transgenic progeny in which one or both alleles of the endogenous P2X$_3$ gene are disrupted.

7. The method of claim 6, further comprising the step of mating said transgenic mice to produce a transgenic mouse homozygous for said P2X$_3$ disrupted allele.

* * * * *